(12) United States Patent
Tackie et al.

(10) Patent No.: US 11,861,298 B1
(45) Date of Patent: Jan. 2, 2024

(54) SYSTEMS AND METHODS FOR AUTOMATICALLY POPULATING INFORMATION IN A GRAPHICAL USER INTERFACE USING NATURAL LANGUAGE PROCESSING

(71) Applicant: TeleTracking Technologies, Inc., Pittsburgh, PA (US)

(72) Inventors: Albert Tackie, Pittsburgh, PA (US); Tejashree Gharat, Pittsburgh, PA (US); Vanita Kolukulri, Pittsburgh, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 288 days.

(21) Appl. No.: 16/166,926

(22) Filed: Oct. 22, 2018

Related U.S. Application Data

(60) Provisional application No. 62/575,349, filed on Oct. 20, 2017.

(51) Int. Cl.
| | | |
|---|---|---|
| *G06F 40/174* | (2020.01) | |
| *G06F 3/16* | (2006.01) | |
| *G10L 15/18* | (2013.01) | |
| *G10L 15/26* | (2006.01) | |
| *G06N 20/00* | (2019.01) | |

(52) U.S. Cl.
CPC ............ *G06F 40/174* (2020.01); *G06F 3/167* (2013.01); *G06N 20/00* (2019.01); *G10L 15/18* (2013.01); *G10L 15/26* (2013.01)

(58) Field of Classification Search
CPC .......... G06F 17/243; G06F 3/16; G06F 3/167; G06F 40/174; G10L 15/26; G10L 15/18; G06N 20/00
See application file for complete search history.

(56) References Cited

U.S. PATENT DOCUMENTS

| | | | |
|---|---|---|---|
| 2005/0071172 A1* | 3/2005 | James | G06F 3/167 704/275 |
| 2010/0131534 A1* | 5/2010 | Takeda | G06F 40/10 707/758 |
| 2014/0101606 A1* | 4/2014 | Albrecht | G06F 40/295 715/803 |
| 2014/0129218 A1* | 5/2014 | Liu | G10L 15/32 704/231 |
| 2014/0379325 A1* | 12/2014 | Houache | G06F 40/274 704/9 |
| 2016/0300573 A1* | 10/2016 | Carbune | G10L 17/22 |

(Continued)

*Primary Examiner* — Jennifer N Welch
*Assistant Examiner* — Parmanand D Patel
(74) *Attorney, Agent, or Firm* — Ference & Associates LLC

(57) ABSTRACT

The present disclosure relates to systems, methods, and computer-readable media for performing natural language processing on a clinical note or audio information associated with medical personnel. A computer-implemented method performed by one or more processors for populating a graphical user interface with data associated with a voice input. The method may include receiving a voice input, generating a first text based on the voice input, comparing the text against a computer model, identifying a data field in the text, selecting a form field based on the identified data field, extracting a second text based on the generated text, and populating the second text in the selected form field.

18 Claims, 6 Drawing Sheets

(56) References Cited

U.S. PATENT DOCUMENTS

| | | | |
|---|---|---|---|
| 2017/0345105 A1* | 11/2017 | Isaacson | H04L 63/06 |
| 2017/0372700 A1* | 12/2017 | Volkov | G10L 15/26 |
| 2018/0240038 A1* | 8/2018 | Adibowo | G06N 20/00 |
| 2018/0314975 A1* | 11/2018 | Zang | G06N 20/20 |

* cited by examiner

300

Patient File  302

First Name [        ]  304   MI [  ]     ID [        ]
Last Name  [        ]        Suffix [  ]

Gender [        ] 306        Assigned Doctor [        ]
Date of Birth [        ]      Previous Hospital
SSN [        ]                [              ▼]
Address [        ]  ZIP [  ]
                              [        ]
Phone [        ]
                              [    ]

Patient John S. Doe was transferred from Grace Hospital.

There are no changes to his health history.

The patient will be discharged tomorrow.

Patient File     402

First Name: John    404    MI: S.    ID:

Last Name: Doe    Suffix:

Gender:

Date of Birth:

SSN:

Address:    ZIP:

Phone:

Assigned Doctor:

Previous Hospital: Grace Hospital

Date for Discharge: 09/15/2017

FIG. 4B

SYSTEMS AND METHODS FOR AUTOMATICALLY POPULATING INFORMATION IN A GRAPHICAL USER INTERFACE USING NATURAL LANGUAGE PROCESSING

PRIORITY CLAIM

This application claims priority from U.S. Provisional Application No. 62/575,349, filed Oct. 20, 2017, which is hereby incorporated by reference in its entirety.

TECHNICAL FIELD

Embodiments of the present disclosure are directed to performing natural language processing on a clinical note or audio information associated with medical personnel. More particularly, disclosed embodiments are directed to automatically populating information on graphical user interfaces using natural language processing.

BACKGROUND

Practitioners, nurses, and medical staff rely on manual data entry into electronic forms for updating patient and facility information. Nurses and staff may write down or manually enter their observations and conversations and enter relevant information from these encounters with physicians and patients into the system forms to track patient transfers, surgeries, and other milestones in patient flow. Manual data entry is time-consuming, prone to user error, and may not encompass all the data the medical staff may wish to associate with the electronic form.

In view of these drawbacks of current systems, improvements in computer systems for natural language processing population of form fields are desired.

SUMMARY

In view of the foregoing, embodiments of the present disclosure describe systems, methods, and computer-readable media for performing natural language processing on a clinical note or audio information associated with medical personnel. More particularly, disclosed embodiments are directed to automatically populating information on graphical user interfaces using natural language processing In one embodiment, the present disclosure describes a computer-implemented method performed by one or more processors for populating a graphical user interface with data associated with a voice input. The method may include receiving a voice input, generating a first text based on the voice input, comparing the text against a computer model, identifying a data field in the text, selecting a form field based on the identified data field, extracting a second text based on the generated text, and populating the second text in the selected form field.

The computer model may be trained on a machine learning system. The method may further include converting the voice input to text on an application programming interface. The computer model may include a natural language processing model. The computer model may include a plurality of models, the plurality of models including at least one of a lexical parser, a gender classifier, a part of speech tagger, a named entity recognizer, and a conference resolution mapper. The method may further include storing the voice input in a memory. The method may further include populating a date and/or a time in a form field based on algorithm calculation. The method may further include fragmenting a sentence in a text. The method may further include assigning a value to a fragment. The method may further include ranking at least one model based on analyzation of voice input.

In another embodiment, the present disclosure describes a non-transitory computer-readable medium storing instructions which, when executed, cause one or more processors to perform a computerized method for populating a graphical user interface with data associated with a conversation. The method may include receiving a voice input, generating a first text based on the voice input, comparing the text against a computer model, identifying a data field in the text, selecting a form field based on the identified data field, extracting a second text based on the generated text, and populating the second text in the selected form field.

The computer model may be trained on a machine learning system. The method may further include converting the voice input to text on an application programming interface. The computer model may include a natural language processing model. The computer model may include a plurality of models, the plurality of models including at least one of a lexical parser, a gender classifier, a part of speech tagger, a named entity recognizer, and a conference resolution mapper. The method may further include storing the voice input in a memory. The method may further include populating a date and/or a time in a form field based on algorithm calculation. The method may further include fragmenting a sentence in a text. The method may further include assigning a value to a fragment. The method may further include ranking at least one model based on analyzation of voice input.

In another embodiment, the present disclosure describes a system for populating a graphical user interface with data associated with a conversation. The system may include an audio sensor, a memory storing instructions, a database comprising a natural language processing model, and a processor configured to execute the stored instructions to perform operations. The operations may include receiving a voice input, generating a first text based on the voice input, comparing the text against the natural language processing model, identifying a data field in the text, selecting a form field based on the identified data field, extracting a second text based on the generated text, and populating the second text in the selected form field. The computer model may include a plurality of models, the plurality of models including at least one of a lexical parser, a gender classifier, a part of speech tagger, a named entity recognizer, and a conference resolution mapper.

It is to be understood that the foregoing general description and the following detailed description are example and explanatory only and are not restrictive of the disclosed embodiments.

BRIEF DESCRIPTION OF THE DRAWINGS

FIG. 3 illustrates an exemplary user interface, consistent with disclosed embodiments, for displaying the automatically populated patient information in a graphical user interface.

FIG. 4A is an example of clinical note for performing natural language processing.

FIG. 4B illustrates another exemplary user interface, consistent with disclosed embodiments, for displaying the automatically populated patient information in a hospital form, based on the clinical note having undergone natural language processing.

DETAILED DESCRIPTION

Reference will now be made in detail to exemplary embodiments, examples of which are illustrated in the accompanying drawing and disclosed herein. Wherever convenient, the same reference numbers will be used throughout the drawings to refer to the same or like parts.

Figure 1:
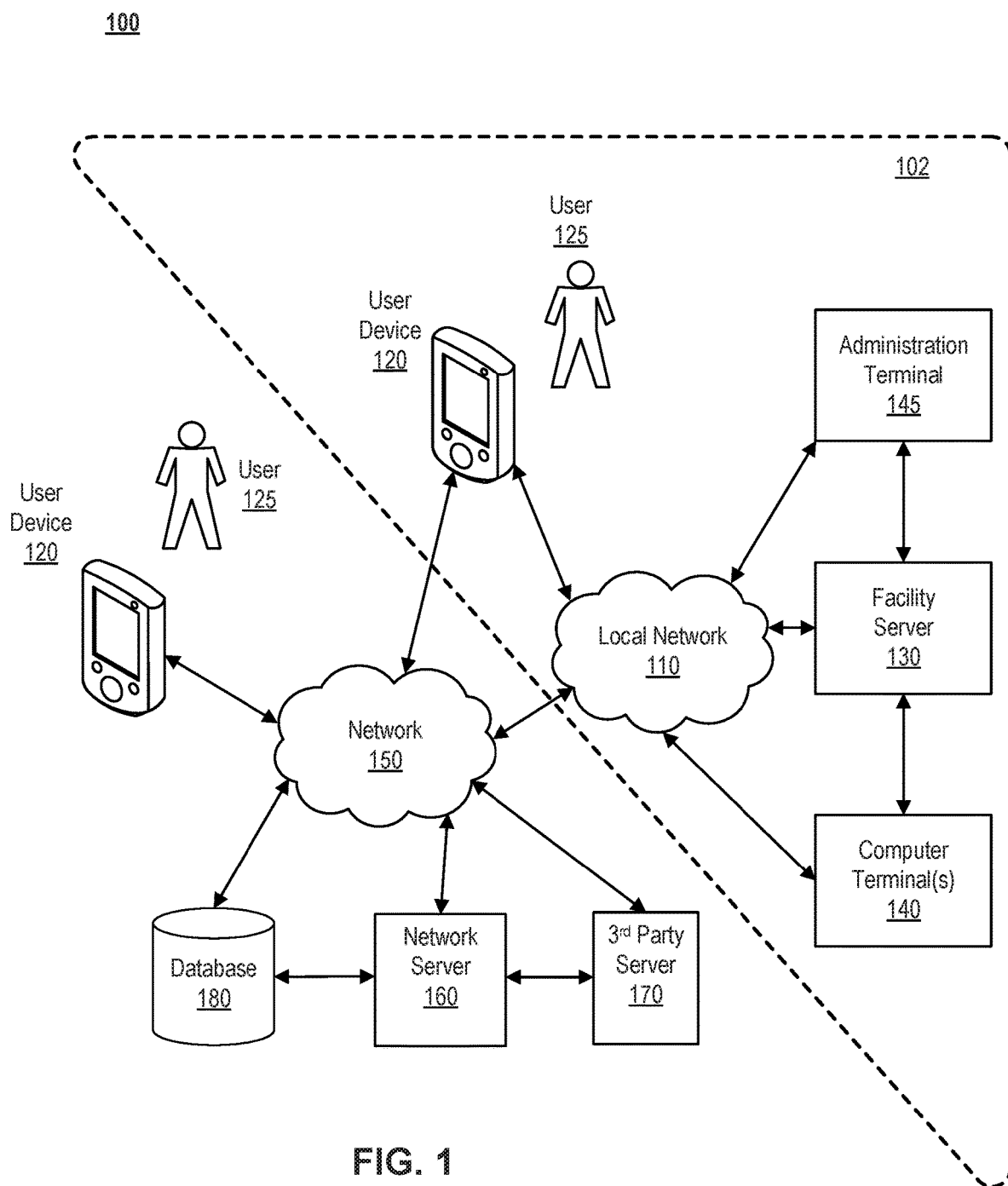
FIG. 1 is block diagram of an exemplary system for automatically populating data based on natural language processing, consistent with embodiments of the present disclosure.

FIG. 1 shows a diagram of a data population and natural language processing system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, data population and natural language processing system 100 may include a facility server 130, a computer terminal 140, an administration terminal 145, one or more user devices 120, network server 160, third party server 170, and database 180. The components of system 100 may communicate directly, through network 150, through local network 110, or through a combination of communications methods. In some embodiments, local network 110, facility server 130, computer terminal 140, administrator terminal 145, and at least one user device 120 may be physically disposed within a facility such as a hospital or office building (i.e. as facility system 102) while at least one user device 120, network 150, network server 160, third party server 170, and database 180 may be external to the workplace. Other components known to one of ordinary skill in the art may be included in system 100 to perform tasks consistent with the disclosed embodiments. For example, in some embodiments, facility system 102 may include one or more sensor devices located throughout the facility to monitor one or more conditions such as occupancy, temperature, humidity, proximity, and other parameters indicative of a status or condition of a bed, room, area, equipment, or supplies. Additionally, in some embodiments facility system 102 may include one or more wireless receivers (not shown) configured to detect one or more wireless sensor or locating tags, to track a location of a tagged item and/or person, or a condition about the tagged item and/or person.

Computer terminal 140 may be a standalone device disposed in an office, a room, an employee station, or an alternative central location in a workplace. In some embodiments, computer terminal 140 may be a desktop or notebook computer, a flat panel or projected display, or any other display. In some embodiments, computer terminal 140 may be associated with a particular room in a facility, such as a particular patient room, hotel room, conference room, or any other type of room. Thus, a message received from a computer terminal 140 may automatically associate the message with the room in which computer terminal 140 is installed.

Administrator terminal 145 may include computer system or device associated with a user 125 that manages or oversees a portion of facility system 102. For example, administrator terminal 145 may comprise a computer system located at a head nurse station, a housekeeping manager's office, or any other department manager's office or station.

Users 125 may be one or more individuals, such as hospital employees and caregivers, associated with the patient. Users 125 may operate computer terminal 140, user devices 120, and/or another computer (not shown) to interact with system 100. Users 125 may be individuals located within and/or outside of the facility system 102. For example, users 125 may include physicians and nurses within the facility responsible for transferring the patients to different units. Users 125 may also include one or more individuals who are responsible for responding to task requests, such as cleaning and transportation of the patients. Users 125 may also include individuals outside of facility system 102, such as people with personal relationships with the patients (e.g. family members) and referring individuals (e.g. outside physicians and medics).

System 100 may be customizable and provide individualized access for each of the users 125. For example, only certain users 125, such as physicians and nurses, may be allowed to generate transfer requests. In some embodiments, one or more users 125, such as the patient's primary physician, may be required to authorize all requests. Users 125 solely responsible for specific tasks may have access limited to perform their responsibilities. It is also contemplated that some users 125, such as family members, may have read-only access.

User devices 120 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, a user device 120 may be a computer system or mobile computer device that is operated by user 125. In some embodiments, a user device 120 may be associated with a particular individual such as user 125, such that messages and/or task assignments directed toward user 125 are sent to user device 120.

In some embodiments, user device 120 may communicate with facility server 130 and/or network server 160 via direct wireless communication links (not shown), or via a combination of one or more of local network 110 and/or network 150.

Facility server 130 may be operated by a facility such as a hospital. Facility server 130 may enable communication within a computer-based system including computer system components such as desktop computers, workstations, tablets, hand held computing devices, memory devices, and/or internal network(s) connecting the components. Thus, in some embodiments facility server 130 may operate as a centralized hub or station for receiving and processing data associated with disclosed methods and techniques, and for generating and sending transmissions associated with disclosed methods and techniques.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local network 110 may comprise any type of computer networking arrangement used to exchange data in a localized area, such as WiFi, Bluetooth™' Ethernet, and other suitable short-range connections that enable computer terminal 140 and user device 120 to send and receive information between the components of system 100. In some embodiments, local network 110 may be excluded, and computer terminal 140 and user device 120 may communicate with system 100 components via network 150. In some embodiments, computer terminal 140 and/or user device 120 may communicate with one or more system 100 components via a direct wired or wireless connection.

Network server 160, third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with a messaging service, such as, for example, Apple Push Notification Service, Azure Mobile Services, or Google Cloud Messaging. In such embodiments, third party server 170 may handle the delivery of messages and notifications related to functions of the disclosed embodiments, such as task creation, task assignment, task alerts, and task completion messages and notifications.

In some embodiments, system 100 may include configurations that vary from the example shown in FIG. 1, which illustrates a facility system 102 working in concert with a cloud computing system including network server 160, third party server 170, and database 180. As a first variation, system 100 may include only facility system 102, and thus may exclude cloud computing components such as network server 160, third party server 170, and database 180. In such embodiments, facility system 102 may handle substantially all operations and functions of the present embodiments. As a second variation, system 100 may exclude components of facility system 102 such as facility server 130. In such embodiments, a cloud computing system including network server 160, third party server 170, and/or database 180 may handle some or all computing and message-related functions of the disclosed embodiments.

Figure 2:
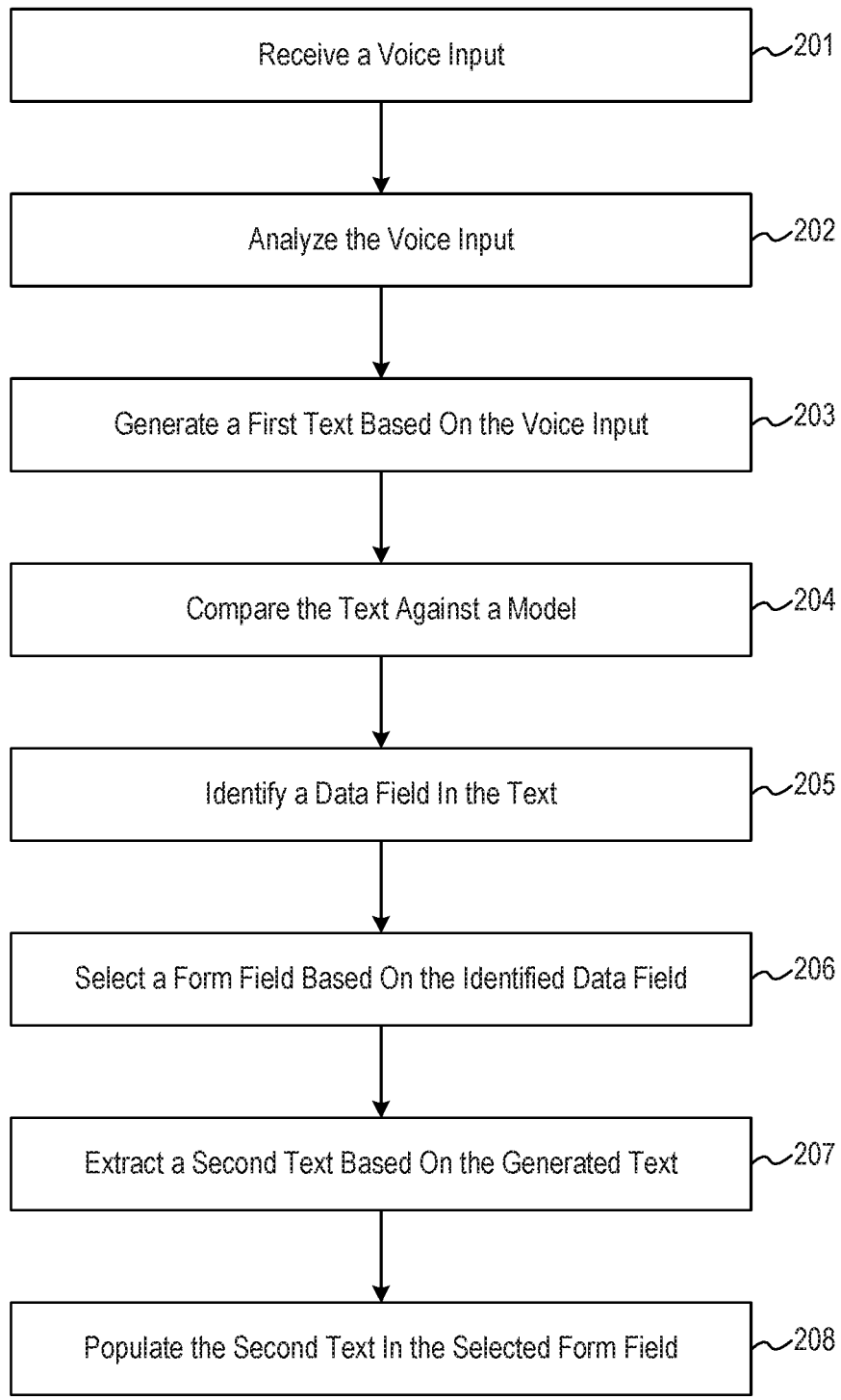
FIG. 2 is a flowchart of an exemplary method for automatically populating data based on natural language processing.

FIG. 2 is a flowchart of an exemplary method 200 for automatically populating data in a data field within a conversation that is recorded as audio data or textual data, consistent with embodiments of the present disclosure. At step 201, a processor (e.g., processor 105) may be configured to receive a voice input. In some embodiments, voice input may be natural language. In other embodiments, the voice input may be human to human conversation. Conversation may be captured by a microphone (e.g., microphone 101) and converted to electrical signal. The microphone (e.g. microphone 101) can take a number of forms including, but not limited to, a microphone of a computer, a microphone of a portable smart device, a standalone microphone, or any other microphones suitable for receiving natural language audio. Furthermore, a filter may be applied to electrical signal, acquired natural language audio, or conversation before converted to electrical signal, in order to reduce noise. At step 202, a processor (e.g., processor 105) may be configured to analyze the voice input. Processor 105 may be configured to analyze the "timbre", that is, the perceived quality of a sound, "pitch", "loudness", and "acoustic fingerprint" of a captured voice. Based on the analyzation, processor 105 may identify the source of voice. For example, a person's voice features, such as, timbre, pitch, acoustic fingerprint, voice pattern, etc., may be stored in a memory and/or a database (e.g., database 109). Processor 105 may compare the voice input with the pre-stored voice features, and may identify a person's voice and a person's location. This may help building more accurate model and reduce errors in the following steps.

After identifying the source of voice input, a processor (e.g., processor 105) may identify relevant models in a database (e.g., database 109) and further rank the models in an order of relevance. At step 203, a processor (e.g., processor 105) may be configured to generate a text based on the voice input by using the models stored in a database (e.g., database 109). Processor 105 may compare the voice input against the models in a database in order and generate a text based on the comparison. Because processor 105 starts from the most relevant model, the efficiency is increased and errors in the generated text may be reduced. At step 204, a processor (e.g., processor 105) may be configured to compare a text against the models stored in a database (e.g., database 109), to identify words in the text. A text may be the generated text based on the voice input or clinical notes, which will be further discussed in FIG. 4A.

At step 205, a processor (e.g., processor 105) may be configured to identify a data field in the text. For example, when "John S. Doe" is in the text, processor 105 may identify "John" as the first name, "Doe" as the last name, and "S" as the middle name. In addition, processor 105 may identify name entities, such as, names of medical facilities, names of diseases, diagnosis, and addresses, etc. Moreover, processor 105 may identify dates and times. For example, when the text contains "Oct. 17, 2017, 08:00 AM", a processor (e.g., processor 105) may identify "Oct. 17, 2017" as date and "08:00" as time. This can be achieved using the models stored in a database. The models may provide the pattern of name entities, dates, and times. For example, capitalized first letter of a word in a sentence may be identified as a pattern of names. And, a pattern of "_/_/__" may be identified as a pattern of dates.

At step 206, a processor (e.g., processor 105) may be configured to select a form field in a hospital form based on the identified data field. For example, when a patient name is identified, then the field for patient name in a hospital form will be selected by a processor. Similarly, when a date is identified, then the field for date in a hospital form will be selected. At step 207, a processor (e.g., processor 105) may be configured to extract words from the generated text or the clinical notes. In a human to human language, a complete sentence, instead of fragmented phrases, is used to convey an idea. Thus, after identifying the meaning of each word in a text, a processor may extract words that are relevant to the selected form fields. For example, when "Patient John S. Doe is transferred to our hospital." is in the text and the form field "patient name" is selected, a processor (e.g., processor 105) may extract "John S. Doe" from the sentence for patient name. At step 208, a processor (e.g., processor 105) may be configured to populate a text in the selected form field. The text may be the extracted words. For example, "John S. Doe" will be populated in the form field "patient name" in the hospital form. Alternatively and concurrently, a processor (e.g., processor 105) may also populate a text from algorithms, which will be further discussed in the following paragraphs.

To identify words and meaning of texts within a conversation, processor 105 may employ one or more computer models (e.g., Lexical parser, gender recognizer, part of speech tagger, conference resolution mapper, named entity recognizer, and natural language processing model, word stemming, etc.) stored in a database (e.g., database 109) for comparing sounds in the received audio information to interpret the audio and to generate text data corresponding to the audio. Different words or phrases with same semantic meaning can be converted or may result in populating a same text in the corresponding form field. For example, English natural language phrases may be: "Patient John S. Doe has been admitted to Stone Oak from Methodist." "Patient John S. Doe has been transferred from Methodist to Stone Oak." "PT (P.T.) John S. Doe has been transferred from Methodist to Stone Oak." "Stone Oak admitting PT. John S. Doe from Methodist." "PT John S. Doe will arrive at Stone Oak from Methodist." And, the corresponding results may be: {$patient_name="John S. Doe", $admitted_hospital="Stone Oak", $transferred_ from ="Methodist"} a processor (e.g., processor 105) may also populate a text from algorithms using the stored models. For example, the text may include "PT John S. Doe is coming in tomorrow." "PT John S. Doe was admitted last month." The corresponding date will be generated by using the algorithm in the models. For example, if it is Jul. 17, 2017 today, then the corresponding result for the date may be: {$date_admitted="Jul. 18, 2017"}, and {$date_admitted="Jun. 17, 2017"}, respectively.

In some embodiments, the processor (e.g. processor 105) may populate a text from stored models. The stored models may include, but are not limited to: speech tagger, conference resolution mapper, named entity recognizer, and natural language processing model, etc. There are several algorithms that may be used in conjunction to generate these models. Lexical parser may be a word tokenizer. Gender classification may be done using pronouns and nouns that associate with an entity. Identifying nouns, pronouns, prepositions, etc. may be done using part of speech tagger. The part of speech tagger may utilize Hidden Markov Models, Dynamic Programming, Supervised Learning and Transformation Based, among others. Nouns can be classified into categories using named entity recognizer (e.g. supervised learning). Coreference Resolution Mapping may be used to associate pronouns with the appropriate entities. Conference Resolution Mapping may utilize Recurrent Neural Networks and Long Short-Term Memory Units. It is helpful in finding the association between entities and when those entities are being referenced. Other algorithms that may be implemented include: N-gram, TF-IDF, word to vector, pairwise ranking, word stemming). Gender classification may be based on using an ensemble of above methods and algorithms.

To extract words from a text, a processor (e.g., processor 105) may compare each word in a text against the models in a database (e.g., database 109) and assign a value to each word. For example, a sentence in a conversation or clinical note may be "John S. Doe has been admitted to Stone Oak.", then a sentence may be tokenized into "John" "S" "." "Doe" "has" "been" "admitted" "to" "Stone" "Oak" "." And, values will be assigned to each token. "John" will be assigned 'first name'. "S" and "." will be assigned "middle name". "Doe" will be assigned "last name". "has", "been", "admitted", and "to" will be assigned '0'. "Stone" and "Oak" will be assigned "hospital name". According to the assigned value, the token with value that is not 0 will be extracted, and then populate in corresponding form fields. The sentence may be tokenized as described here using any of the algorithms or methods discussed herein.

Natural language input such as speech input may be converted to text using an application programming interface (API). Natural Language Processing may be applied to identify data fields in the text including, but not limited to: Patient Name, Location, Physician Name, Diagnoses, Facilities the Patient is being transferred from and to, and other fields discussed herein. Additionally, a machine learning system may be implemented and utilized to improve the accuracy of the text population into the form fields. In some embodiments, the accuracy of what was recognized as the correct data fields to the form fields after the text was generated using Natural Language Processing Models that were trained by the machine learning system on Healthcare text/speech data in healthcare. The machine learning system may store a computer model that, when applied to the natural language input, populates the text into form fields.

The model may be continuously improved when encountered with additional natural language inputs. Additionally, the model may have previously been exposed to an abundance of natural language inputs training the machine learning system and the associated model to match the natural language inputs with form fields based on the text characterization. The model may have been trained by supplying training data sets, validation data sets, and testing data sets. For example, the model may have been created using the training data sets and machine learning algorithms including a corpus of medical terminology including acronyms and short-hand notations for medical terms and form field cues. The generated model may be built using a neural network.

Figure 2A:
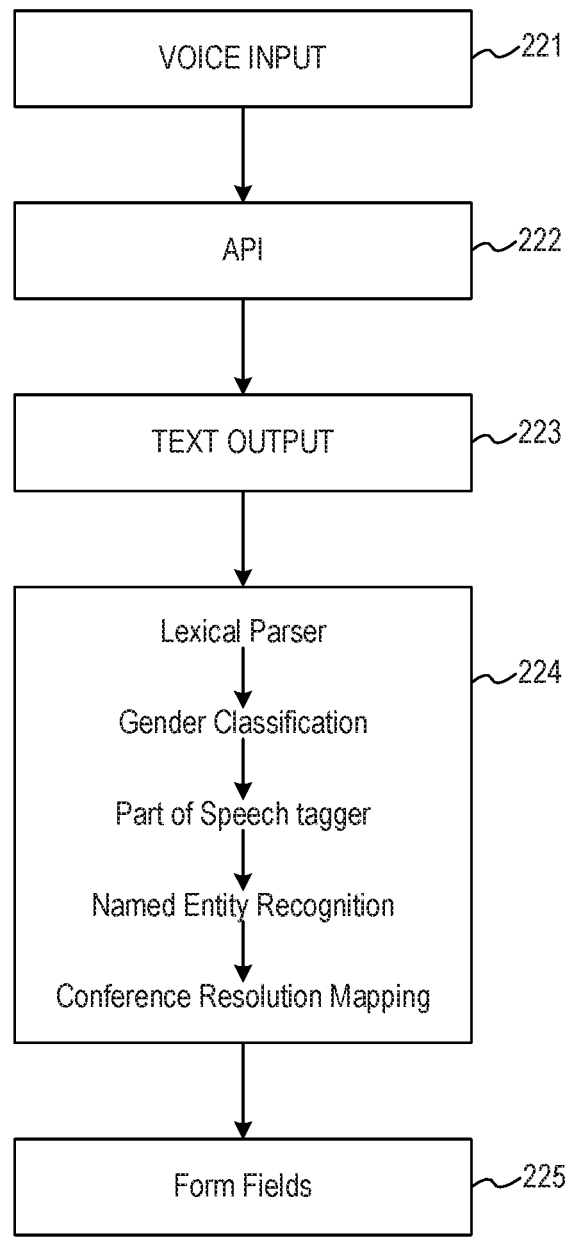
FIG. 2A is a flowchart of an exemplary method for automatically populating data based on natural language processing.

FIG. 2A is a flowchart of an exemplary method 200 for automatically populating data in a data field within a conversation that is recorded as audio data or textual data, consistent with embodiments of the present disclosure. At step 221 a voice input may be obtained such as a natural language of a user. The voice input from step 221 may be transmitted to an API at step 222. The natural language input such as speech input may be converted to text by the API. The API may provide a text output at step 223. At step 224, Natural Language Processing may be applied to identify data fields in the text including, but not limited to: Patient Name, Location, Physician Name, Diagnoses, Facilities the Patient is being transferred from and to, and other fields discussed herein.

Step 224 may apply a number of stored models to the text output from step 223. As discussed herein, the stored models may include, but are not limited to: speech tagger, conference resolution mapper, named entity recognizer, and natural language processing model, etc. There are several algorithms that may be used in conjunction to generate these models. Lexical parser may be a word tokenizer. Gender classification may be done using pronouns and nouns that associate with an entity. Identifying nouns, pronouns, prepositions, etc. may be done using part of speech tagger. The part of speech tagger may utilize Hidden Markov Models, Dynamic Programming, Supervised Learning and Transformation Based, among others. Nouns can be classified into categories using named entity recognizer (e.g. supervised learning). Coreference Resolution Mapping may be used to associate pronouns with the appropriate entities. Conference Resolution Mapping may utilize Recurrent Neural Networks and Long Short-Term Memory Units. It is helpful in finding the association between entities and when those entities are being referenced. Other algorithms that may be implemented include: N-gram, TF-IDF, word to vector, pairwise ranking, word stemming). Gender classification may be based on using an ensemble of above methods and algorithms. Based on the Natural Language Processing, the text from the text output may be populated into form fields at step 225.

FIG. 3 illustrates an exemplary user interface, consistent with disclosed embodiments, for displaying the automatically populated patient information in a hospital form. In FIG. 3, an exemplary hospital form 300 may include a plurality of form fields. For example, form field 302 represents where the patient's first name should be filled in, form field 304 represents where the patient's last name should be filled in, form field 306 represents where the patient's gender should be filled in, and so on.

FIG. 4A is an example of clinical note. And, corresponding to the clinical note in FIG. 4A, FIG. 4B illustrates the automatically populated patient information in a hospital form. In FIG. 4A, date, time, and patient information are written in English natural language in the clinical note. The clinical note is then read into a system for automatically populating data within a conversation, consistent with the disclosed embodiments. Using the method described above, a form in FIG. 4B is automatically filled out corresponding to the information provided in the clinical note. For example, in hospital form 400, form field for "First name" 402 is filled with John, corresponding to the text in the clinical note in FIG. 4A; form field for "Last name" 404 is filled with Doe, corresponding to the text in the clinical note in FIG. 4A. Additionally, form field for "Date for discharge" is filled with Sep. 15, 2017, even if the "date for discharge" is not directly disclosed in the clinical note. Based on "The patient will be discharged tomorrow." which is written in the clinical note in FIG. 4A, a processor (e.g., processor 105) may identify "tomorrow" as a phrase for a date. After calculation, processor 105 may populate "Sep. 15, 2017" in the form field for "Date for discharge", based on "Sep. 14, 2017", which is the date written in the clinical note.

Figure 5:
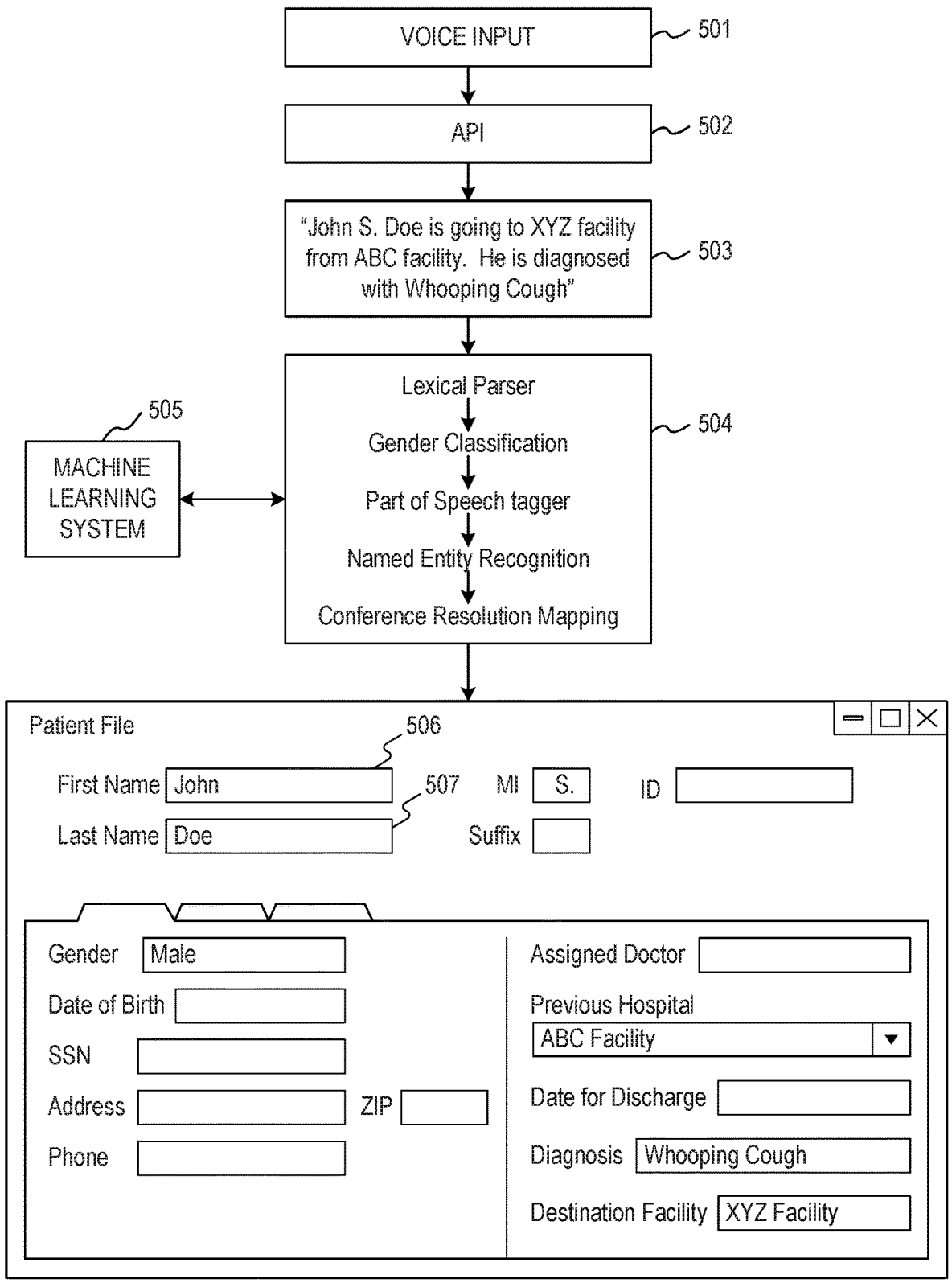
FIG. 5 is a flowchart of an exemplary method for automatically populating data based on natural language processing including an exemplary user interface, consistent with disclosed embodiments, for displaying the automatically populated patient information in a hospital form, based on the clinical note having undergone natural language processing.

FIG. 5 illustrates an exemplary method 500 for automatically populating data in a data field within a conversation that is recorded as audio data or textual data, consistent with embodiments of the present disclosure. At step 501 a voice input may be obtained such as a natural language of a user. The voice input from step 501 may be transmitted to an API at step 502. The natural language input such as speech input may be converted to text by the API. The API may provide a text output at step 503. Step 503 provides a non-limiting example of a text output from the API, "John S. Doe is going to XYZ facility from ABC facility. He is diagnosed with Whooping Cough". This text was generated as a result of the natural language input to the API. At step 504, Natural Language Processing may be applied to identify data fields in the text including, but not limited to: Patient Name, Location, Physician Name, Diagnoses, Facilities the Patient is being transferred from and to, and other fields discussed herein.

Step 504 may apply a number of stored models to the text output from step 223. As discussed herein, the stored models may include, but are not limited to: speech tagger, conference resolution mapper, named entity recognizer, and natural language processing model, etc. There are several algorithms that may be used in conjunction to generate these models. Lexical parser may be a word tokenizer. Gender classification may be done using pronouns and nouns that associate with an entity. Identifying nouns, pronouns, prepositions, etc. may be done using part of speech tagger. The part of speech tagger may utilize Hidden Markov Models, Dynamic Programming, Supervised Learning and Transformation Based, among others. Nouns can be classified into categories using named entity recognizer (e.g. supervised learning). Coreference Resolution Mapping may be used to associate pronouns with the appropriate entities. Conference Resolution Mapping may utilize Recurrent Neural Networks and Long Short-Term Memory Units. It is helpful in finding the association between entities and when those entities are being referenced. Other algorithms that may be implemented include: N-gram, TF-IDF, word to vector, pairwise ranking, word stemming). Gender classification may be based on using an ensemble of above methods and algorithms.

Additionally, a machine learning system 505 may be implemented and utilized to improve the accuracy of the text population into the form fields. In some embodiments, the accuracy of what was recognized as the correct data fields to the form fields after the text was generated using Natural Language Processing Models that were trained by the machine learning system on Healthcare text/speech data in healthcare. The machine learning system may store a computer model that, when applied to the natural language input, populates the text into form fields.

The model may be continuously improved when encountered with additional natural language inputs. Additionally, the model may have previously been exposed to an abundance of natural language inputs training the machine learning system and the associated model to match the natural language inputs with form fields based on the text characterization. The model may have been trained by supplying training data sets, validation data sets, and testing data sets. For example, the model may have been created using the training data sets and machine learning algorithms including a corpus of medical terminology including acronyms and short-hand notations for medical terms and form field cues. The generated model may be built using a neural network.

Based on the Natural Language Processing, the text from the text output may be populated into form fields such as the first name field 506 and the last name filed 507. Additional fields may be filled depending on the text input provided. In this example, the Natural Language Processing may result in the gender field, the previous hospital field, the diagnosis field, and the destination facility field being filled.

Based on above, the disclosed system and method populates information in a hospital form automatically. A user may either speak to the disclosed system or enter a clinical note into the disclosed system, and the system may automatically populate information in the corresponding form fields in a hospital form. This may reduce time and effort for a healthcare provider to fill in the patient information in hospital forms. And, in turn, a healthcare provider may concentrate on more important tasks; thus, increases the quality of service.

The invention claimed is:

1. A computer-implemented method which, when executed, causes one or more processors to perform the computer-implemented method for populating a graphical user interface with data associated with a voice input, the method comprising:
receiving a voice input, wherein the receiving comprises identifying, by analyzing characteristics of the voice input, a source of the voice input;

generating a first text based on the voice input, wherein the generating comprises comparing the voice input against at least one computer model selected based upon a source of the voice input;

identifying, for each word in the first text, a meaning of each of the words in the first text;

identifying a plurality of data fields within a form to be populated with text from the first text;

identifying, for each of the words in the first text using the at least one computer model trained on a machine learning system and identifying entity patterns, a data field of the plurality of data fields to be populated with at least one of the words within the first text, wherein a data field of the plurality of data fields is identified based upon the meanings of each of the words; and populating the plurality of data fields with the words in the first text, wherein the populating comprises identifying at least one words within the first text does not match an entity pattern for the corresponding of the plurality of data fields and populating the corresponding of the plurality of data fields with a second text different than the at least one words within the first text and matching the entity pattern for the corresponding of the plurality of data fields, wherein the second text is generated based on inferring, by employing one or more computer models, the second text from one of the first text and the received voice input based upon the meaning of the at least one words within the first text and wherein the second text is not directly disclosed in the first text and the received voice input.

2. The computer implemented method of claim 1 further comprising:
converting the voice input to text on an application programming interface.

3. The computer implemented method of claim 1 wherein: the at least one computer model comprises a natural language processing model.

4. The computer implemented method of claim 1 wherein: the at least one computer model comprises a plurality of models, the plurality of models comprising a lexical parser, a gender classifier, a part of speech tagger, a named entity recognizer, and a conference resolution mapper.

5. The computer implemented method of claim 1, further comprising: storing the voice input in a memory.

6. The computer implemented method of claim 1, further comprising: populating a date and/or a time in a form field based on algorithm calculation.

7. The computer implemented method of claim 1, further comprising: fragmenting a sentence in a text.

8. The computer implemented method of claim 7, further comprising: assigning a value to a fragment.

9. The computer implemented method of claim 1, further comprising: ranking the at least one computer model based on analyzation of voice input.

10. A non-transitory computer-readable medium storing instructions which, when executed, cause one or more processors to perform a computerized method for populating a graphical user interface with data associated with a conversation, comprising:
receiving a voice input, wherein the receiving comprises identifying, by analyzing characteristics of the voice input, a source of the voice input;

generating a first text based on the voice input, wherein the generating comprises comparing the voice input against at least one computer model selected based upon a source of the voice input;

identifying, for each word in the first text, a meaning of each of the words in the first text;

identifying a plurality of data fields within a form to be populated with text from the first text;

identifying, for each of the words in the first text using the at least one computer model trained on a machine learning system and identifying entity patterns, a data field of the plurality of data fields to be populated with at least one of the words within the first text, wherein a data field of the plurality of data fields is identified based upon the meanings of each of the words; and populating the plurality of data fields with the words in the first text, wherein the populating comprises identifying at least one words within the first text does not match an entity pattern for the corresponding of the plurality of data fields and populating the corresponding of the plurality of data fields with a second text different than the at least one words within the first text and matching the entity pattern for the corresponding of the plurality of data fields, wherein the second text is generated based on inferring, by employing one or more computer models, the second text from one of the first text and the received voice input based upon the meaning of the at least one words within the first text and wherein the second text is not directly disclosed in the first text and the received voice input.

11. The non-transitory computer-readable medium of claim 10 further comprising:
converting the voice input to text on an application programming interface.

12. The non-transitory computer-readable medium of claim 10 wherein:
the at least one computer model comprises a natural language processing model.

13. The non-transitory computer-readable medium of claim 10 wherein:
the at least one computer model comprises a plurality of models, the plurality of models comprising a lexical parser, a gender classifier, a part of speech tagger, a named entity recognizer, and a conference resolution mapper.

14. The non-transitory computer-readable medium of claim 10, further comprising: populating a date and/or a time in a form field based on algorithm calculation.

15. The non-transitory computer-readable medium of claim 10, further comprising: fragmenting a sentence in a text.

16. The non-transitory computer-readable medium of claim 15, further comprising: assigning a value to a fragment.

17. A system for populating a graphical user interface with data associated with a conversation, the system comprising:
an audio sensor;
a memory storing instructions;
a database comprising at least one computer model; and
a processor configured to execute the stored instructions to perform operations comprising:
receiving a voice input, wherein the receiving comprises identifying, by analyzing characteristics of the voice input, a source of the voice input;
generating a first text based on the voice input, wherein the generating comprises comparing the voice input against the at least one computer model selected based upon a source of the voice input;
identifying, for each word in the first text, a meaning of each of the words in the first text;

identifying a plurality of data fields within a form to be populated with text from the first text;

identifying, for each of the words in the first text using the at least one computer model trained on a machine learning system and identifying entity patterns, a data field of the plurality of data fields to be populated with at least one of the words within the first text, wherein a data field of the plurality of data fields is identified based upon the meanings of each of the words; and populating the plurality of data fields with the words in the first text, wherein the populating comprises identifying at least one words within the first text does not match an entity pattern for the corresponding of the plurality of data fields and populating the corresponding of the plurality of data fields with a second text different than the at least one words within the first text and matching the entity pattern for the corresponding of the plurality of data fields, wherein the second text is generated based on inferring, by employing one or more computer models, the second text from one of the first text and the received voice input based upon the meaning of the at least one words within the first text and wherein the second text is not directly disclosed in the first text and the received voice input.

18. The system of claim 17 wherein:

the at least one computer model comprises a plurality of models, the plurality of models comprising a lexical parser, a gender classifier, a part of speech tagger, a named entity recognizer, and a conference resolution mapper.

* * * * *